(12) United States Patent
Zurbrick

(10) Patent No.: US 6,946,670 B1
(45) Date of Patent: Sep. 20, 2005

(54) EFFECTIVE SCANNING RESOLUTION ENHANCEMENT

(75) Inventor: Larry Zurbrick, San Jose, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 98 days.

(21) Appl. No.: 10/674,898

(22) Filed: Sep. 30, 2003

(51) Int. Cl.$^7$ ............................................. G01N 21/86
(52) U.S. Cl. ............... 250/559.06; 250/234; 356/237.2
(58) Field of Search ......... 250/559.06, 559.45–559.48, 250/234; 356/237.2, 237.3, 237.4, 237.5; 348/125–126

(56) References Cited

U.S. PATENT DOCUMENTS

| | | | |
|---|---|---|---|
| 5,736,735 A | * | 4/1998 | Hagiwara .................... 250/225 |
| 5,932,871 A | * | 8/1999 | Nakagawa et al. ........ 250/201.3 |
| 6,654,110 B2 | * | 11/2003 | Yonezawa et al. ........ 356/237.2 |

* cited by examiner

*Primary Examiner*—David Porta
*Assistant Examiner*—Patrick J. Lee
(74) *Attorney, Agent, or Firm*—Luedeka, Neely & Graham, P.C.

(57) ABSTRACT

An inspection system to inspect structures on a substrate. A generator directs a primary beam at the substrate along a selectable angle, thereby producing a secondary beam having properties that are characteristic of the structures on the substrate. At least one of the substrate and the primary beam are scanned relative to the other at a selectable speed. A sensor receives the secondary beam and provides analog signals having properties that are characteristic of the secondary beam. An analog to digital converter receives the analog signals and provides digital signals having properties that are characteristic of the analog signals. A controller receives the digital signals and determines the properties of the structures on the substrate based at least in part on the properties of the digital signals.

19 Claims, 1 Drawing Sheet

EFFECTIVE SCANNING RESOLUTION ENHANCEMENT

FIELD

This invention relates to the field of integrated circuit fabrication. More particularly, this invention relates to instrumentation used for inspecting integrated circuits and related tooling and equipment.

BACKGROUND

The integrated circuit fabrication industry relies on frequent and accurate inspections of integrated circuits and tooling to ensure that the integrated circuits are fabricated properly. Because of the extremely small size of the structures of which integrated circuits are formed, the inspection techniques used must be extremely precise and accurate. Furthermore, as the size of such structures is continually decreased over time, the inspection techniques are required to keep pace by resolving smaller and smaller structures.

One method of structure inspection is an optical technique where a beam of some kind is directed toward the structure, and then the properties of the beam are analyzed as it is either reflected by or transmitted through the structure. For example, a mask or other substrate can be inspected by scanning the substrate underneath a beam that is directed at its surface. Typically, the substrate is moved in one direction within its plane, which direction of movement is defined as the X direction. The beam is then scanned back and forth across the substrate in a direction that is transverse to the direction in which the substrate is moving, which transverse direction is defined as the Y direction. In this manner, the beam makes a raster scanning pattern across the substrate, and can be directed at one time or another to impinge upon all or any desired portion of the substrate.

As mentioned above, the beam may either transmit through the substrate or be reflected by the substrate, either in whole or in part. The beam that is initially directed toward the substrate is called the primary beam herein. The transmitted beam or the reflected beam, as appropriate for the given inspection tool, is called the secondary beam herein. The secondary beam is detected by one or more sensors, which detect one or more characteristics of the secondary beam. For example, the degree to which the secondary beam is scattered as it is reflected by a substrate tends to contain information in regard to the shape and other properties of the structures formed on the substrate.

However, an inspection tool built to measure the size of structures fabricated within a certain range of dimensions may not be able to adequately measure the size of structures fabricated within a smaller range of dimensions. Thus, as structure size continually decreases with the desired increase in integrated circuit density, there is a tendency for the inspection equipment to become outdated, typically long before it is worn out or otherwise depleted. The need to replace such outdated equipment tends to generally increase the cost of fabricating integrated circuits.

One way to increase the resolution of an inspection tool is to operate the sensing mechanisms at a higher sampling frequency. However, this approach usually requires a considerable amount of work to redesign the analog electronics, system clock synchronization, and analog to digital converters. At the currently required frequencies of more than seventy-five megahertz, such system alternations are difficult and time consuming to engineer and test, perhaps requiring a year or more to accomplish.

What is needed, therefore, is a system to more rapidly extend the utile life of an inspection system.

SUMMARY

The above and other needs are met by an inspection system adapted to inspect structures on a substrate. A beam generator directs a primary beam at the substrate at a selectable scanning angle, thereby producing a secondary beam having properties that are characteristic of properties of the structures on the substrate. Means are used to scan at least one of the substrate and the primary beam relative to the other at a selectable speed. A sensor receives the secondary beam and provides analog signals having properties that are characteristic of the properties of the secondary beam. An analog to digital converter receives the analog signals and provides digital signals having properties that are characteristic of the properties of the analog signals. A controller preferably adjusts the selectable scanning angle and the selectable speed, receives the digital signals, and determines the properties of the structures on the substrate based at least in part on the properties of the digital signals.

By having the ability to vary the scanning angle to a selectable value in this manner, the effective sampling rate of the inspection system can be adjusted without redesigning the electronics of the inspection system, such as the analog electronics, system clock synchronization, and analog to digital converters. Thus, by increasing the effective sampling rate, the resolution of the inspection system is increased without an engineering redesign of the system, and the utile life of the inspection system can be increased to some degree. This is made possible by effectively increasing the number of sample readings within a given area by scanning the primary beam along the substrate at an angle other than ninety degrees to the direction of substrate travel, while preferably commensurately decreasing the speed at which the substrate is moved forward through the primary beam.

In various preferred embodiments, the beam is a laser beam, but could also be a different kind of beam, such as but not limited to an electron beam or an ion beam. The selectable scanning angle is preferably between about forty-five degrees and about ninety degrees, and is most preferably about forty-five degrees. The selectable speed is preferably equal to cosine of ninety degrees minus the selectable scanning angle, times a nominal speed used when the selectable scanning angle is ninety degrees. The substrate is preferably a mask for an integrated circuit layer. In some embodiments the secondary beam is a reflected beam, and in some embodiments the secondary beam is a transmitted beam.

According to another aspect of the invention there is described a method to inspect structures on a substrate. A primary beam is directed at the substrate at a selectable scanning angle, thereby producing a secondary beam having properties that are characteristic of properties of the structures on the substrate. The substrate is held underneath the primary beam, and at least one of the substrate and the primary beam are scanned relative to the other at a selectable speed. The secondary beam is received and analog signals are provided having properties that are characteristic of the properties of the secondary beam. The analog signals are received and digital signals are provided having properties that are characteristic of the properties of the analog signals. The properties of the structures on the substrate are determined based at least in part on the properties of the digital signals.

BRIEF DESCRIPTION OF THE DRAWINGS

Further advantages of the invention are apparent by reference to the detailed description when considered in conjunction with the figures, which are not to scale so as to more clearly show the details, wherein like reference numbers indicate like elements throughout the several views, and wherein.

DETAILED DESCRIPTION

Figure 1:
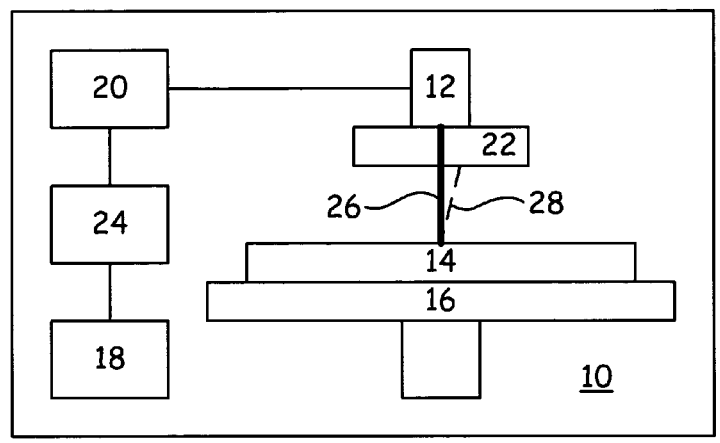
FIG. 1 is a functional block diagram of an inspection system according to a preferred embodiment of the invention.

With reference now to FIG. 1 there is depicted a functional block diagram of an inspection system 10 according to a preferred embodiment of the invention. The inspection system 10 is adapted for sensing the properties of structures on a substrate 14, such as the width of features on a mask, reticle, or integrated circuit formed on a silicon wafer, for example. The substrate 14 is preferably retained in the inspection system 10 such as by a substrate stage 16. A primary beam 26 is directed toward the surface of the substrate 14 by a beam generator 12, and the beam 26 and the substrate 14 are scanned, one relative to the other.

It is appreciated that there are a variety of methods by which the primary beam 26 and the substrate 14 can be moved relative to each other to accomplish the desired scanning of the substrate 14. For example, the beam generator 12 can be placed on a stage that moves the beam 26 across the surface of the substrate 14 in a single scan line, and then indexes the beam generator 12 down the length of the substrate 14 by one scan line width, and then scan back in the other direction, while the substrate 14 remains motionless relative to the rest of the system 10. Alternately, the stage 16 could accomplish the same relative motion by moving the substrate 16 while the beam generator 12 is held still relative to the rest of the system 10.

Most preferably, some of the desired motion is produced by moving the substrate 14 with the stage 16, and the rest of the desired motion in produced by deflecting the primary beam 26 in a desired direction while holding the beam generator 12 motionless relative to the rest of the inspection system 10. In this preferred embodiment, an optical system is used to scan the primary beam 26 relative to the substrate 14 in one direction, which as mentioned above is defined as the Y direction. The stage 16 then preferably indexes the substrate 14 under the beam 26 in the X direction as each pass of the primary beam 26 is accomplished in the Y direction. In this manner, selected portions of the substrate 14, and preferably all of the substrate 14, can be inspected by the system 10 as desired.

The primary beam 26 is preferably of a type that has properties which change when the beam 26 contacts the surface of or passes through the substrate 14, and a secondary beam 28 is produced. The secondary beam 28 may be a reflected beam, such as is depicted in FIG. 1, or alternately a transmitted beam, or may also included both reflected and transmitted components. Most preferably the secondary beam 28 is a reflected beam, and the primary beam 26 is a laser beam. However, it is appreciated that other combinations of primary beam 26 types and secondary beam 28 types, whether reflected or transmitted, are also contemplated herein.

In the case where the primary beam 26 is a laser beam and the secondary beam 28 is a reflected beam, a substrate 14 can be inspected for a variety of structural and other properties by sensing properties of the reflected beam 28 with one or more sensors 22. For example, some properties of the reflected beam 28 that can be detected are the degree of scattering, phase, and the degree of extinction of the reflected beam 28. Properties of the secondary beam 28 such as these can be interpreted to indicate properties of the structures on the substrate 14, such as where one material on the surface of the substrate 14 stops and another material on the surface of the substrate starts. Thus, such an inspection system 10 can be used, for example, to determine line widths of structures on the substrate 14, and contaminates on the surface of the substrate 14.

The sensor 22 is preferably a high speed photodiode, which produces analog signals that have properties that are characteristic of the properties of the secondary beam 28. The analog signals are preferably amplified, and are then received and digitized by an analog to digital converter 20, which preferably operates at a given sampling frequency. Most preferably the sampling frequency of the analog to digital converter is a set value because, as mentioned above, changing the sample frequency tends to require a large amount of design work. However, in alternate embodiments the sampling frequency is variable.

The analog to digital converter 20 provides digital signals that have properties that are characteristic of the properties of the analog signals, and thus the properties of the digital signals are also characteristic of the properties of the secondary beam 28, which in turn indicates that the properties of the digital signals are characteristic of the properties of the structures on the substrate 14. The digital signals are received by a controller 24, which interprets the digital signals and thus determines the properties of the structures on the substrate 14, based at least in part on the properties of the digital signals. The controller 24 may also use other information about the substrate 14 in making this determination, which information can be received through an input 18.

Figure 2:
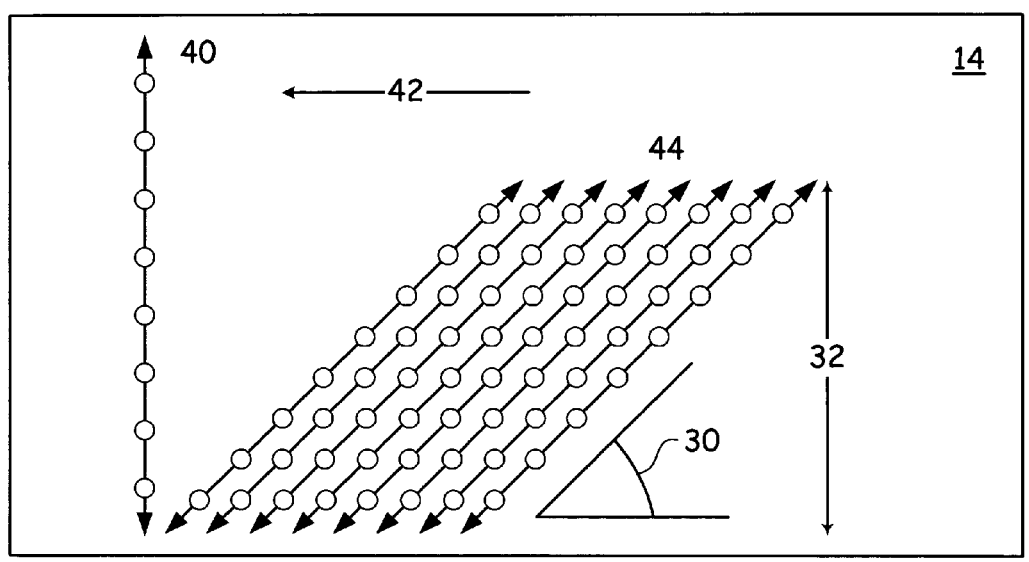
FIG. 2 is a diagrammatic representation of the a primary beam scanning across a substrate at a selectable scanning angle.

Most preferably, the controller 24 is able to control a selectable scanning angle 30 at which the primary beam 26 is scanned across the surface of the substrate 14, as depicted in FIG. 2. As mentioned above, the primary beam 26 is typically scanned in a Y direction 40 that is transverse to the travel of the substrate 14 in the X direction 42, or in other words is at a ninety degree angle to the X direction 42. However, in a preferred embodiment of the present invention, the primary beam 26 is scanned in the Y direction along a path 44 that is at an angle 30 to the X direction 42 of travel of the substrate 14. Preferably, the angle 30 is variable between about ninety degrees and about forty-five degrees, but may in some embodiments be variable to an angle 30 which is even less than about forty-five degrees.

Additionally, the controller 24 is also preferably able to control a selectable speed at which the substrate 14 is moved along the X direction 42. These two variable parameters, scanning angle 30 and substrate speed, enable the inspection system 10 to provide greater effective sampling frequencies without changing the clocking of the analog to digital converter 20 or other elements of the digitizer channel, and thus without incurring the investment in engineering design which that requires. Thus, the inspection system 10 is able to resolve somewhat smaller features, which tends to lengthen the utile life of the inspection system 10.

In one embodiment both the selectable scanning angle 30 and the selectable substrate speed are entered into the inspection system 10, such as through the input 18. In other embodiments the selectable scanning angle 30 is entered via the input 18, and the controller 24 then determines the appropriate substrate speed as described below. In yet other embodiments, a desired resolution is entered through the input 18, and the controller 24 then determines the appropriate scanning angle 30 and substrate speed. The selectable scanning angle 30 and the selectable substrate speed may be input manually, such as by a technician who is operating the inspection system 10, or may be input automatically from a remote engineering database of recipes, or program sets, under which the inspection system 10 operates.

By adjusting the selectable scanning angle 30 and the selectable substrate speed in this manner, the effective number of samples per unit area can be increased. The manner in which this is accomplished is depicted in FIG. 2., with an example of adjusting the scanning angle 30 from a ninety degree angle as given along path 40 to a forty-five degree angle as given along paths 44. The path 40 is the path that is typically used to sweep the primary beam 26. In this example, the digitizer channel is set to take eight sample readings along the depicted distance of the path 40, as represented by the circles drawn along the path 40. It is appreciated that there are many different methods by which the number of sample readings may be set. For example, the primary beam 26 may scan the path 40 repeatedly and at a very fast rate, while the sensor 22 is programmed to take readings at given time intervals which are known to coincide with desired positions of the primary beam 26 on the substrate 14.

By adjusting the scanning angle 30 to forty-five degrees, for example, the new scanning path for the primary beam 26 is along the paths 44, with each incremental path 44 representing another scan of the primary beam 26 as the substrate 14 is indexed forward in the direction of travel 42. By adjusting the scanning angle 30 in this manner, it can be seen that the eight sample readings taken along the length of any given one of the scanning paths 44 are now disposed within a distance 32 that is somewhat reduced from the length of the original scanning path 40. In other words, a greater number of sample readings has been taken within the distance 32 than previously was accomplished within the same distance along the path 40.

By adjusting the substrate speed as the scanning angle 30 is adjusted, the locations of the sample readings from consecutive scanning paths 44 can be aligned in a transverse direction, to form an effectual scanning path that uses sample readings from several different scans 44, and which effectual scanning path includes a higher density of sample readings than the path 40. Thus, the resolution of the scanning process has been increased in both the X and the Y directions by adjusting the scanning angle 30 and the substrate speed, and no adjustment to the digitizer channel was required.

The controller 24 is preferably programmed to receive the sample readings taken from the new paths 44, and with a knowledge of the selectable scanning angle 30 and substrate speed, is able to reorder the data so as to produce an orthogonal array of data, rather than the nonorthogonal configuration of the data as collected in the scanning paths 44. In this manner the data, or the results of the scanning, are presented in a configuration that is the same as what the tool operator is accustomed to seeing.

Thus, one purpose of this invention is to increase the number of samples per spot in a laser based image scanner such as that found in the 300-series and "slf" series tools manufactured by KLA-Tencor Technologies Corporation of San Jose, Calif. The increased samples per spot is preferred when inspecting 1) smaller line widths (at a minimum pitch consistent with the spot size), or 2) phase shift masks with greater frequency content in their optical frequency spectrum.

This invention increases the Y direction samples per spot by intentionally scanning the sample substrate at an acute angle relative to the X stage motion through the rotation of the scanning beam using the beam scan rotation optics (dove prism for the KLA-Tencor 3xx equipment, and the K-mirror for the KLA-Tencor slf equipment). Normal operation of the image scanner sets the Y direction scanning beam at a nominal ninety degree angle with respect to the X stage scanning direction. The preferred scanning angle described herein is forty-five degrees with respect to the stage X scanning direction. This allows an increase in samples per spot of 1.4 (square root of two) times the current sample rate in the Y direction. Increased samples per spot in the X axis is accomplished by decreasing the X stage scanning velocity by a similar amount. The resulting data stream is then "re-sorted" by one of several methods. In the case of contamination inspection (such as STARlight inspection), it may not be necessary to re-sort the incoming data stream. The stripe (i.e. scan) swath heights also decrease similar amounts resulting in increases in the minutes per square centimeter specification for system throughput.

In some embodiments the method according to the present invention may require a pre-processing of the input data stream to re-sort data into the standard orthogonal data representation. The data re-sort is accomplished in one embodiment by writing data into a random access memory buffer in the "diagonal" scan orientation direction and reading the data from the buffer in a normal scan "orthogonal" direction. In another embodiment the data is written into a buffer in a data "orthogonal" direction and then read out of the buffer in a "diagonal" direction so as to reorient the data.

The beam rotation subsystem is preferably adjusted to set the scanning direction to forty-five degrees with respect to the X stage direction. It is noted that the dove prism or K-mirror would preferably has a rotation of only half the desired angle 30, or 22.5 degrees in the preferred embodiment. The method does not depend on whether the rotation Y direction scan leads or lags behind X stage motion. Digitized data values are preferably written into an m by n buffer, where m refers to rows of memory and n refers to columns of memory, so that the first valid data value is written to the memory location "D" indicated by $D_{m,n}$. The next data value is written to $D_{m+i,n+i}$. In general, the data writes are written to memory as $D_{m+j,n+j}$ where i=0,1,2,3 .... Data is preferably read from memory as $D_{m+j}$. The X stage scan velocity is preferably adjusted to 0.707 times the velocity normally for the given pixel size (meaning the normal scan pixel size).

It is noted that the inspected "care area" is preferably compensated in size (or ramp distance) so that full swath height data is built up by the edge of the intended care area. Partial height data in the buffer is preferably disregarded.

The foregoing description of preferred embodiments for this invention has been presented for purposes of illustration and description. It is not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. An inspection system adapted to inspect structures on a substrate, the inspection system comprising:
   a beam generator adapted to direct a primary beam at the substrate at a variable scanning angle as defined by X and Y coordinates and not by an angle of incidence of the primary beam on the substrate, thereby producing a secondary beam having properties that are characteristic of properties of the structures on the substrate,
   a stage adapted to scan the substrate relative to the primary beam at a selectable speed, where a direction of movement of the stage is defined as the X coordinate, and the Y coordinate is perpendicular to the X coordinate within a plane of the substrate,
   a sensor adapted to receive the secondary beam and provide analog signals having properties that are characteristic of the properties of the secondary beam,
   an analog to digital converter adapted to receive the analog signals and provide digital signals having properties that are characteristic of the properties of the analog signals, and
   a controller adapted to receive the digital signals and determine the properties of the structures on the substrate based at least in part on the properties of the digital signals, and to selectively order the digital signals in an output based on a relationship between the variable scanning angle and the selectable speed, where a resolution of the inspection system is variable based on the variable scanning angle and the selectable speed.

2. The inspection system of claim 1, wherein the variable angle is between about forty-five degrees and about ninety degrees.

3. The inspection system of claim 1, wherein the variable angle is about forty-five degrees.

4. The inspection system of claim 1, wherein the selectable speed is equal to about cosine of ninety degrees minus the variable angle, times a nominal speed used when the variable angle is ninety degrees.

5. The inspection system of claim 1, wherein the secondary beam is a reflected beam.

6. The inspection system of claim 1, wherein the substrate is a semiconductor wafer.

7. The inspection system of claim 1, wherein the substrate is a mask for an integrated circuit layer.

8. An inspection system adapted to inspect structures on a substrate, the inspection system comprising:
   a beam generator adapted to direct a primary beam at the substrate at an adjustable angle as defined by X and Y coordinates and not by an angle of incidence of the primary beam on the substrate, thereby producing a secondary beam having properties that are characteristic of properties of the structures on the substrate,
   means for adjusting a selectable angle at which the primary beam scans on the substrate,
   a substrate stage adapted to hold the substrate underneath the primary beam, where a direction of relative movement between the stage and the primary beam is defined as the X coordinate, and the Y coordinate is perpendicular to the X coordinate within a plane of the substrate,
   means for scanning at least one of the substrate and the primary beam relative to the other at a selectable speed,
   an input adapted to receive the selectable angle and the selectable speed,
   a sensor adapted to receive the secondary beam and provide analog signals having properties that are characteristic of the properties of the secondary beam,
   an analog to digital converter adapted to receive the analog signals and provide digital signals having properties that are characteristic of the properties of the analog signals, and
   a controller adapted to adjust the selectable angle, adjust the selectable speed, receive the digital signals, and determine the properties of the structures on the substrate based at least in part on the properties of the digital signals, and to selectively order the digital signals in an output based on a relationship between the variable scanning angle and the selectable speed, where a resolution of the inspection system is variable based on the variable scanning angle and the selectable speed.

9. The inspection system of claim 8, wherein the beam is a laser beam.

10. The inspection system of claim 8, wherein the selectable angle is between about forty-five degrees and about ninety degrees.

11. The inspection system of claim 8, wherein the selectable angle is about forty-five degrees.

12. The inspection system of claim 8, wherein the selectable speed is equal to about cosine of ninety degrees minus the selectable angle, times a nominal speed used when the selectable angle is ninety degrees.

13. The inspection system of claim 8, wherein the substrate is a semiconductor wafer.

14. The inspection system of claim 8, wherein the substrate is a mask for an integrated circuit layer.

15. The inspection system of claim 8, wherein the secondary beam is a reflected beam.

16. A method to inspect structures on a substrate, the method comprising the steps of:
   directing a primary beam at the substrate at a selectable angle as defined by X and Y coordinates and not by an angle of incidence of the primary beam on the substrate, thereby producing a secondary beam having properties that are characteristic of properties of the structures on the substrate,
   scanning at least one of the substrate and the primary beam relative to the other at a selectable speed and in a direction, where the selectable angle is not ninety degrees relative to the direction, where the direction is defined as the X coordinate, and the Y coordinate is perpendicular to the X coordinate within a plane of the substrate,
   receiving the secondary beam and providing analog signals having properties that are characteristic of the properties of the secondary beam,
   receiving the analog signals and providing digital signals having properties that are characteristic of the properties of the analog signals,
   determining the properties of the structures on the substrate based at least in part on the properties of the digital signals, and
   selectively ordering the digital signals in an output based on a relationship between the variable scanning angle and the selectable speed, where a resolution of the inspection method is variable based on the variable scanning angle and the selectable speed.

17. The method of claim 16, wherein the primary beam is a laser beam.

18. The method of claim 16, wherein the secondary beam is a reflected beam.

19. The method of claim 16, wherein the selectable angle is about forty-five degrees.

* * * * *